United States Patent
Booij et al.

(10) Patent No.: US 10,368,783 B2
(45) Date of Patent: Aug. 6, 2019

(54) POSITION DETERMINATION SYSTEM

(71) Applicant: Sonitor Technologies AS, Oslo (NO)

(72) Inventors: Wilfred Edwin Booij, Nordby (NO); Oystein Haug Olsen, Asker (NO)

(73) Assignee: Sonitor Technologies AS, Oslo (NO)

( * ) Notice: Subject to any disclaimer, the term of this patent is extended or adjusted under 35 U.S.C. 154(b) by 398 days.

(21) Appl. No.: 15/066,763

(22) Filed: Mar. 10, 2016

(65) Prior Publication Data

US 2016/0192864 A1 Jul. 7, 2016

Related U.S. Application Data

(62) Division of application No. 13/880,928, filed as application No. PCT/GB2011/052033 on Oct. 20, 2011, now Pat. No. 9,310,207.

(30) Foreign Application Priority Data

Oct. 20, 2010 (GB) .................... 1017711.1

(51) Int. Cl.
*A61B 5/11* (2006.01)
*H04W 64/00* (2009.01)
(Continued)

(52) U.S. Cl.
CPC ............ *A61B 5/1113* (2013.01); *A61B 5/002* (2013.01); *A61B 5/0026* (2013.01); *A61B 5/1117* (2013.01); *A61B 5/6801* (2013.01); *A61B 5/6824* (2013.01); *A61B 5/7246* (2013.01); *A61B 5/7282* (2013.01); *A61B 5/746* (2013.01); *G01C 5/06* (2013.01); *G01C 21/005* (2013.01); *G01C 21/206* (2013.01); *G01S 5/00* (2013.01); *G01S 5/0257* (2013.01); *G01S 5/18* (2013.01); *G08B 21/043* (2013.01); *G08B 21/18* (2013.01);
(Continued)

(58) Field of Classification Search
CPC ...... G01C 21/005; G01C 5/06; G01C 21/206; A61B 5/1113; A61B 5/1117; A61B 5/7246; A61B 5/746; A61B 5/7282; A61B 5/002; A61B 5/0026; A61B 5/6801; A61B 2560/0223
USPC ........................................ 702/138
See application file for complete search history.

(56) References Cited

U.S. PATENT DOCUMENTS 5,210,540 A  5/1993 Masumoto
5,652,592 A  7/1997 Rouquette
(Continued)

FOREIGN PATENT DOCUMENTS

FR  2486662  1/1982
FR  2888940  1/2007
(Continued)

OTHER PUBLICATIONS

Bunter Adrian WO 2009150251 A2, Dec. 2009 Machine Translation.*
Chinese office action for CN20118058498.1 dated Feb. 4, 2017.

*Primary Examiner* — Yoshihisa Ishizuka
(74) *Attorney, Agent, or Firm* — O'Shea Getz P.C.

(57) ABSTRACT

A monitoring system is provided that includes a three dimensional position determination system for determining the three dimensional coordinates of one or more mobile units. The system includes at least one zone in which the system is arranged to raise an alarm when the rate of change of a vertical coordinate of a mobile unit is less than a predetermined value.

18 Claims, 2 Drawing Sheets

(51) Int. Cl.
*H04W 48/04* (2009.01)
*A61B 5/00* (2006.01)
*G01C 5/06* (2006.01)
*G01C 21/20* (2006.01)
*G01S 5/00* (2006.01)
*G01S 5/02* (2010.01)
*G08B 21/04* (2006.01)
*G01C 21/00* (2006.01)
*G08B 21/18* (2006.01)
*G01S 5/18* (2006.01)

(52) U.S. Cl.
CPC ........... *H04W 48/04* (2013.01); *H04W 64/00* (2013.01); *A61B 2560/0223* (2013.01); *A61B 2560/0242* (2013.01); *A61B 2562/0247* (2013.01)

(56) References Cited

U.S. PATENT DOCUMENTS

| | | | |
|---|---|---|---|
| 6,160,478 A | 12/2000 | Jacobsen et al. | |
| 6,196,355 B1 * | 3/2001 | Fargo | B66B 3/00 187/287 |
| 6,333,694 B2 | 12/2001 | Pierce et al. | |
| 6,518,918 B1 | 2/2003 | Vannucci et al. | |
| 2002/0016694 A1 * | 2/2002 | Tsuji | G01C 5/06 702/138 |
| 2008/0010013 A1 * | 1/2008 | Rusanen | B66B 1/34 701/408 |
| 2008/0088706 A1 * | 4/2008 | Girgensohn | H04N 5/247 348/207.99 |
| 2009/0014254 A1 * | 1/2009 | Finschi | B66B 1/468 187/381 |
| 2009/0121940 A1 | 5/2009 | Ladd et al. | |
| 2009/0322548 A1 | 12/2009 | Gottlieb | |
| 2010/0052896 A1 | 3/2010 | Goodman | |

FOREIGN PATENT DOCUMENTS

| | | | |
|---|---|---|---|
| JP | 2001245027 | 9/2001 | |
| JP | 2004045284 | 2/2004 | |
| JP | 2004220241 | 8/2004 | |
| JP | 2006228024 | 8/2006 | |
| JP | 2008241467 | 10/2008 | |
| JP | 2009281741 | 12/2009 | |
| JP | 2009301450 | 12/2009 | |
| WO | 0058744 | 10/2000 | |
| WO | WO 2009150251 A2 * | 12/2009 | ........... B66B 5/0025 |

* cited by examiner

POSITION DETERMINATION SYSTEM

This application is a divisional of U.S. patent application Ser. No. 13/880,928 filed Aug. 9, 2013, which entitled to the benefit of, and incorporates by reference essential subject matter disclosed in PCT Application No. PCT/GB2011/052033 filed on Oct. 20, 2011, which claims priority to Great Britain Application No. 1017711.1 filed Oct. 20, 2010, all of which are herein incorporated by reference.

BACKGROUND OF THE INVENTION

1. Technical Field

The invention relates to a position determination system for determining the position of one or more mobile units with respect to one or more fixed position base units.

2. Background Information

Indoor real-time location systems (RTLS) can operate with different levels of accuracy depending on the system infrastructure. In general, a real time location system can provide a 3 dimensional position (e.g. x, y and z coordinates) using for example triangulation on ultrasound or radio frequency (RF) signal amplitudes (e.g. from a Wi-Fi infrastructure). However, when deployed in a single floor, it is not normally possible to determine an accurate vertical (z) coordinate. An accurate vertical coordinate can be obtained by installing significant additional infrastructure. For example, with additional infrastructure, three dimensional coordinates can be determined to centimeter accuracy. However this additional infrastructure can be very costly.

In some scenarios there is high value in fixing the position along the vertical axis. For example in a home care or hospital setting it is essential to quickly establish if a patient has collapsed or fallen on the ground. It is sufficient to know which room the patient is in when lying on the floor, i.e. the horizontal (x, y) plane does not need to be determined to high accuracy, while the vertical (z) axis needs to differentiate between the patient lying on the floor and sitting in a chair. This is contrary to the accuracy of a normal indoor real time location system which provides high accuracy in the horizontal plane while providing low accuracy in the vertical axis.

Accelerometers may appear appealing at first sight, but such an inertial system also requires attitude estimation (using gyros) and becomes rapidly complex. An inertial system would also need to be on all the time in order to integrate the acceleration to achieve velocity and position and would thus draw too much power for a battery powered tag.

SUMMARY OF THE DISCLOSURE

According to a first aspect, the invention provides a position determination system comprising one or more fixed base units and one or more mobile units, wherein the system is arranged to determine the horizontal position of a mobile unit based on the proximity of said mobile unit to at least one base unit and wherein the system is arranged to determine a vertical position of said mobile unit based on the air pressure sensed at the mobile unit and the air pressure sensed at one or more of the base units.

Thus the base units and mobile units comprise means for determining air pressure e.g. air pressure sensors. By using air pressure sensors to determine the height (i.e. the vertical axis position or z-ordinate) of the mobile unit, the system can avoid the additional complexity and expense of the additional infrastructure described above. Although air pressure sensors need to be introduced into the system, these can be introduced into the existing units, i.e. the mobile units and base units. Installation of further base units is not required to increase the vertical accuracy of the system.

In fact, although many systems may want to retain an accurate position determination in the horizontal (x, y) plane (e.g. to centimeter accuracy as described above), the system allows the system hardware to be reduced further where this is not required. For example, as mentioned above, in some circumstances room level accuracy is sufficient. This can be achieved with only a single base unit in each room. The base unit can simply determine the presence or absence of a mobile unit. Alternatively, even if more than one base unit can detect the mobile unit, the position can easily be determined to room level based on signal strength. In other arrangements it may be possible to use only one base unit per floor.

By measuring the air pressure at the base unit which is in a fixed (static) position at a known height, and measuring the air pressure at the mobile unit which is mobile and at a variable height, the difference in pressure can be determined and thereby a difference in height can be calculated. Therefore the height of the mobile unit relative to the known height of the base unit can be determined.

Recently, inexpensive low-power air pressure sensors have become available that can provide up to 10 cm height accuracy (i.e. they can detect the pressure change caused by 10 cms of vertical movement). In the case of a mobile tag worn on a patient's arm, this accuracy is sufficient to distinguish between the situations where the patient is sitting in a chair and lying on the floor.

The air pressure sensor readings may inherently drift slowly over time. This can lead to inaccurate height determinations and consequently incorrect situation analysis (either false positives or false negatives). Sensor readings may drift due to changes in air pressure and also due to changes in temperature or mechanical stress within the sensor. For example pressure sensors are typically made using silicon microsystem technology and stresses can arise from differences in expansion coefficients between the materials that the pressure sensor is made of, e.g. between the packaging and the sensor itself. This drift is inherent to the sensor. Therefore preferably the position determination system comprises a plurality of base units and the system is arranged to determine a reference pressure based on an average of the pressures sensed at each of the plurality of base units. By combining the readings from multiple base units, the inherent sensor drift can be averaged out in order to provide the overall reference pressure. Depending on the infrastructure employed in the system, the readings from all base units may be combined or the base units may be formed into groups (for example one group per floor) and the readings of each group combined to provide a plurality of reference pressures.

The air pressure sensor readings in the mobile units can also drift over time. It is not practical to provide multiple pressure sensors in each mobile unit, so the above averaging scheme cannot be employed. The mobile units could simply be calibrated manually at regular intervals to ensure readings are accurate. However, preferably the position determination system comprises at least one height reference base unit and the system is arranged such that when a mobile unit is determined to be within a certain proximity of said height reference base unit the system determines that the mobile unit is at a predetermined mobile unit reference height. In response to said proximity determination, the system may instruct the mobile unit to perform a calibration based on the mobile unit reference height.

To explain further, in certain situations a mobile unit can be assumed to be within a certain narrow height band. For example, when a patient is passing through a door or along a corridor it can be assumed that the patient is walking. Therefore a mobile unit worn on a person's arm is at a fairly consistent height above ground. At such times, the height of the mobile unit is known and the current air pressure at that height is known from the base units, so the pressure sensor in the mobile unit can be calibrated to be consistent with the base units. This may be done by sending correction information to the mobile unit or it may be done by storing correction information elsewhere within the system to be applied to all pressure data collected from that mobile unit.

Preferably the mobile unit can be instructed to increase a communication rate when in close proximity to the height reference base unit. This allows the system to detect the point at which the mobile unit and the base unit are closest which will allow a more accurate calibration to be performed. When the units are closest together, the pressure-height relationships at the two locations will be most similar.

The predetermined height may be different for each tag. For example, people can be different heights. Therefore mobile units (tags) worn by those people will be positioned at different heights above ground. Consequently, when those people pass through the calibration zone, the calibration will need to take into account those different heights. Preferably each mobile unit for use with the system has a unique identifier and the system can determine which mobile unit is passing the height reference base unit. The system can then look up the identifier in a database in order to find the expected height of that mobile unit in order to perform the calibration correctly. In alternative embodiments, the expected height of each mobile unit may be programmed into the respective mobile unit. Calibration can then be effected either by transmitting the expected height data from the mobile unit to the base unit or by transmitting pressure data from the base unit to the mobile unit. Processing for performing the calibration calculations can be carried out either on the mobile unit, on the base unit or on a separate processor connected to the system.

In some arrangements the system may comprise a height calibration zone. Said height calibration zone could be any height determination system which can establish a height of the mobile unit. The height determination system may comprise a plurality of base units positionally arranged so as to be capable of determining the height of a mobile unit based on the proximity of said mobile unit to each of said plurality of base units. In this way an accurate vertical axis position can be obtained without use of the pressure sensors. In response to said height determination, the system may instruct the mobile unit to perform a calibration based on a determined height of the mobile unit and/or a reference pressure. The calibration may be performed on a server or within the mobile unit as discussed in more detail later. Although this arrangement requires the extra infrastructure for accurate vertical axis determination, that infrastructure is only required in the location of the calibration zone, not throughout the system. The additional cost is therefore minimized.

Preferably the system is arranged to raise an alarm based on one or more criteria being met by the system. More preferably, one of the criteria involves information taken from a mobile unit. The alarm could take the form of an audible alert (e.g. a siren), a visual alert (e.g. flashing light), or an alert on a computer system (which can notify one or more users of the system). The alarm could also take the form of paging one or more persons (e.g. medical staff) or telephoning one or more persons (e.g. relatives or friends) and playing a recorded message. Preferably the alarm is arranged to indicate an identification of the mobile unit and a current position of the mobile unit. This enables the alarm respondents to proceed to the location of the particular mobile unit quickly and efficiently.

Preferably one alarm criterion is based on the current height of the mobile unit. As described above, in a medical or care environment this criterion can be used to detect a patient collapsing or falling to the floor. Another alarm criterion may be based on a threshold amount, a difference of height and/or rate of change of height of said mobile unit: e.g. a sudden change of height can be indicative of a patient collapsing.

In preferred embodiments the criteria depend on the current position of said mobile unit. For example, if the system is being used to detect patient emergencies by detecting a patient collapsing, it is important to distinguish certain zones such as stairs where a patient (and corresponding mobile unit) should be allowed to descend to and below the floor level without raising an alarm. Similarly, a patient may sink rapidly into a chair or onto a bed when there is no emergency situation.

In such situations, a number of different data can be combined to make a more accurate determination of an alarm situation. For example, the height data can be combined with the height change data to establish for example if a patient descended rapidly, but not to floor level, or if the patient descended to floor level slowly and deliberately (e.g. to pick something up or to look under a bed). In situations which are unclear, further data may be gathered as described in more detail below.

The base unit and the mobile unit may be arranged to communicate via ultrasound—i.e. they are provided with respective ultrasound transmitters and/or receivers. Alternatively or additionally, the base unit and the mobile unit may be arranged to communicate via radio communication i.e. they are provided with respective radio transmitters and/or receivers. In either case communications may be one way or two way. Different communication set-ups may be preferred in different situations. For example, radio waves can pass through solid objects more readily than ultrasound waves. In situations where position determination is to be carried out on a room-level within a building, ultrasound may be preferred as sensors in neighboring rooms are less likely to detect a mobile unit. Electromagnetic radiation can also interfere with important equipment within a hospital or care environment, again favoring ultrasound. Alternatively, in irregularly-shaped rooms or where many obstructing objects may be located, electromagnetic radiation may be preferred.

The height determination of the mobile unit may be based on pressure data combined with height determination based on proximity to the base units. For example, a crude estimation of height may be obtained based on location relative to the base units (e.g. by triangulation or trilateration) without using the pressure data. The pressure data (which is likely to be more accurate) can then be combined with this crude height estimate in order to provide a more precise height determination. The techniques of sensor fusion may be employed in combining the various data.

In preferred embodiments, a stationary mobile unit may be arranged to act as an additional base unit. When the mobile unit is stationary (as determined by a motion sensor or by external position detectors for example), it can essentially provide the same function as a fixed base unit. With this arrangement all stationary mobile units can be used to improve the reference pressure estimation without the complexity and expense involved in adding extra base units to the system.

Preferably, the mobile units and/or the base units comprise temperature sensors. Temperature sensors can be used in the calibration of the pressure sensors.

According to another aspect, the invention provides a mobile unit for use in a position determination system, said mobile unit comprising an air pressure sensor and a transmitter arranged to transmit data from said air pressure sensor to said system. The transmitter may be an ultrasound transmitter.

In some embodiments the mobile unit comprises a receiver and the unit is adapted to transmit position data including at least data from said pressure sensor in response to receipt of an instruction or request signal.

Preferably the mobile unit is adapted to receive a calibration instruction and in response to said calibration instruction the mobile unit is adapted to calibrate the pressure sensor. The calibration instruction may include at least a reference pressure and/or a reference height.

The pressure sensor is preferably capable of determining height (altitude) to the nearest 30 cm, more preferably to the nearest 20 cm, more preferably still to the nearest 10 cm.

The mobile unit and the base units preferably sample the air pressure at regular intervals. The mobile unit may comprise a motion sensor and the mobile unit may be adapted to reduce the frequency of sampling of the air pressure when the motion sensor senses that the mobile unit has not moved for a predetermined time. The frequency may be reduced to zero, but preferably the air pressure is sampled regularly to compensate for drift. When the mobile unit is stationary, all changes in pressure can be assumed to derive from sensor drift or from atmospheric pressure changes.

In preferred embodiments, the mobile unit described above is used as part of the position determination system described above.

According to a further aspect, the invention provides a building comprising a position determination system as described above, the building comprising one or more monitoring zones for positioning mobile units, wherein each monitoring zone comprises at least one base unit. Preferably at least one monitoring zone comprises only one base unit. The one or more monitoring zones may each correspond to a room within the building. A building thus fitted with a position determination system can be used to locate monitoring units to within room accuracy.

Intelligent buildings are becoming more commonplace, with sensors being fitted to more and more components of the building and capable of sending data to a central monitoring station. Such sensors can provide useful further indications of a particular situation and therefore incorporating these sensors into the system logic can provide more reliable situation analysis. This can result in fewer false positive and/or false negative determinations. As an example, a system which determines a patient emergency situation based on the sensed pressure data, can determine that the situation is most likely a false positive if immediately afterwards, the door of the detected room is shut and the light switched off preferably therefore the position determination system is adapted to receive data from one or more sensors within the building, the sensors including at least one of: a light switch sensor, a motion sensor, a door sensor and a telephone activity sensor. Preferably the position determination system is adapted to raise an alarm based on one or more criteria being met by a mobile unit and based on the output of said building sensors.

According to another aspect, the invention provides a method of determining the position of a mobile unit relative to one or more fixed base units, comprising: measuring the air pressure at the position of said mobile unit; measuring the air pressure at the position of said base units; measuring the proximity of the mobile unit to said base units; determining the horizontal position of said mobile unit based on said proximity measurements; and determining the height of said mobile unit based on said air pressure measurements.

It is to be understood that, where preferred features have been described above in relation to one aspect (e.g. the system, mobile unit, building or method), they are equally applicable to all other aspects. The different aspects described above are all inter-related and form part of the same overall system.

Although some of the features above have been described in relation to a hospital or other care environment for detecting patient emergencies, it will be understood that the system can also apply to a large number of other situations.

In one example, the system could be used as part of an equipment or inventory monitoring system for locating specific pieces of equipment or items of stock, and for detecting misplacement of articles. For example, an alarm could be raised if fragile items are detected as moving above a certain height which is considered to be risky.

In one set of embodiments the system is arranged to raise an alarm when a mobile unit is in a predetermined zone and its rate of change of a vertical coordinate is less than a threshold value. The zone may be a stairwell, a ramp or a lift shaft or some other such region of the system premises in which the height of a mobile unit may be expected to change (increase or decrease) at a certain rate. For example in a care environment as described elsewhere in this document, a patient in a stairwell is expected to be ascending or descending the stairs. If a mobile unit attached to the patient indicates that the patient is not changing their vertical coordinate, it may indicate that the patient is in difficulty and an alarm should be raised. As with the other systems described in this document, the horizontal position determination need not be particularly accurate—it could be accurate only to room level (e.g. sufficient to locate the stairwell in which the patient is located).

Such an arrangement is novel and inventive in its own right and thus according to another aspect the invention provides a monitoring system comprising a three dimensional position determination system for determining the three dimensional coordinates of one or more mobile units, said system comprising at least one zone in which the system is arranged to raise an alarm when the rate of change of a vertical coordinate of a mobile unit is less than a predetermined value.

In this system, the vertical coordinate could be determined by any means, e.g. by air pressure sensors as previously described or by means of ultrasound or RF signals.

In a set of embodiments the system according to the aspect of the invention set out above further comprises at least one zone in which the system is arranged to raise an alarm when the rate of change of a vertical coordinate of a mobile unit is greater than a predetermined value. As described elsewhere, the system needs to distinguish between the two types of zone as the conditions for raising an alarm change when the patient moves from one type of zone to the other. In an ordinary room, the patient is expected to remain mostly at a constant height and an alarm should be raised if that height changes rapidly.

BRIEF DESCRIPTION OF THE DRAWINGS

Preferred embodiments of the invention will now be described, by way of example only, and with reference to the accompanying drawings in which.

DETAILED DESCRIPTION OF THE INVENTION

Figure 1:
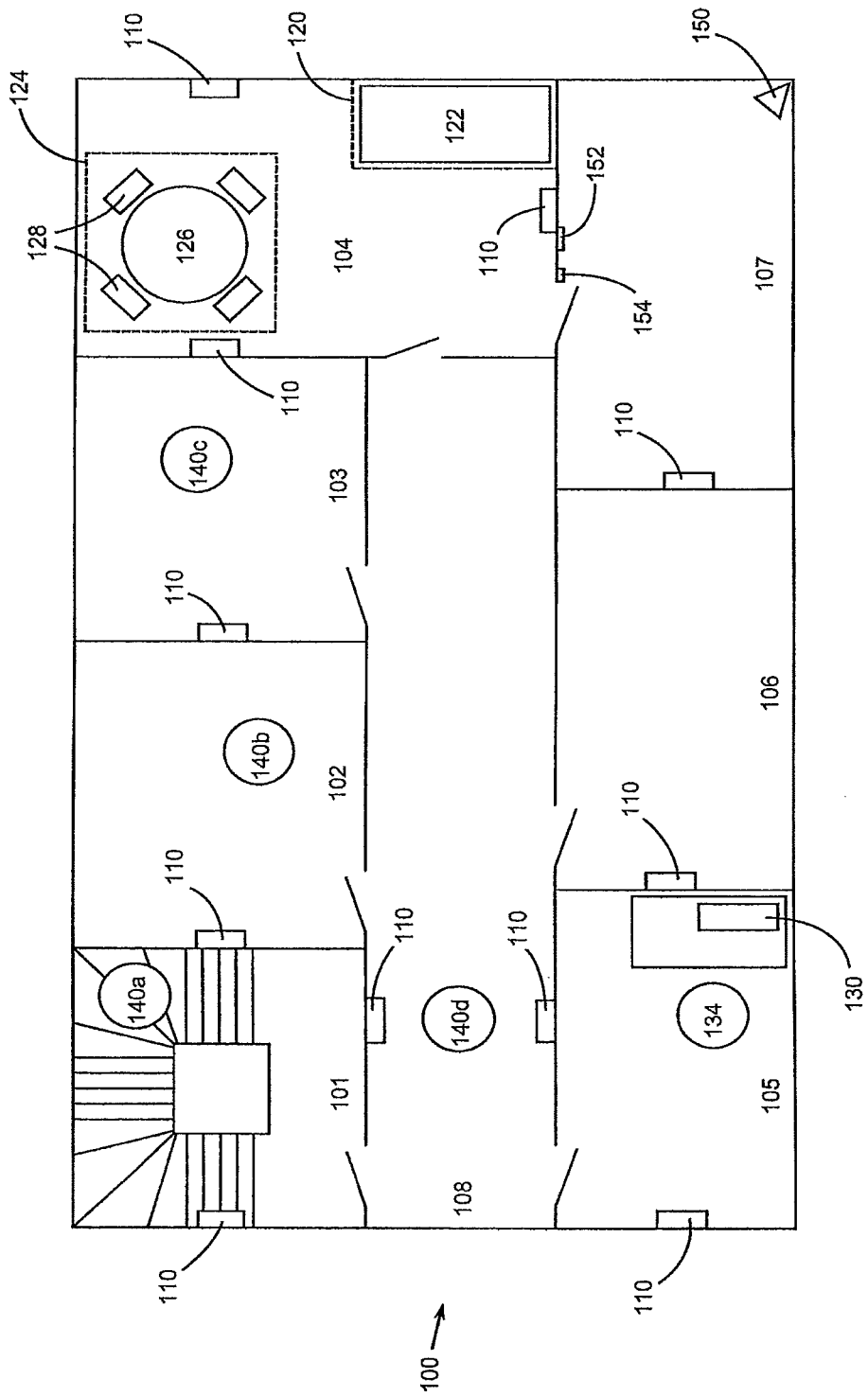
FIG. 1 shows a floor of a building with a location system according to the invention.

FIG. 1 illustrates a floor 100 of a building which has been fitted with a real time location system embodying the invention. The floor 100 is divided into a number of separate spaces 101 to 108. 101 is a stairwell with stairs leading up and/or down to floors above and/or below. 102 to 107 are various rooms and 108 is a corridor. In particular, room 105 is a monitoring room containing a central computer 130 which may be monitored by an operator 134. It should be appreciated however that the computer 130 may be located elsewhere within the building or completely off site, connected to the system through a direct connection, or over a network and/or the internet.

Figure 2:
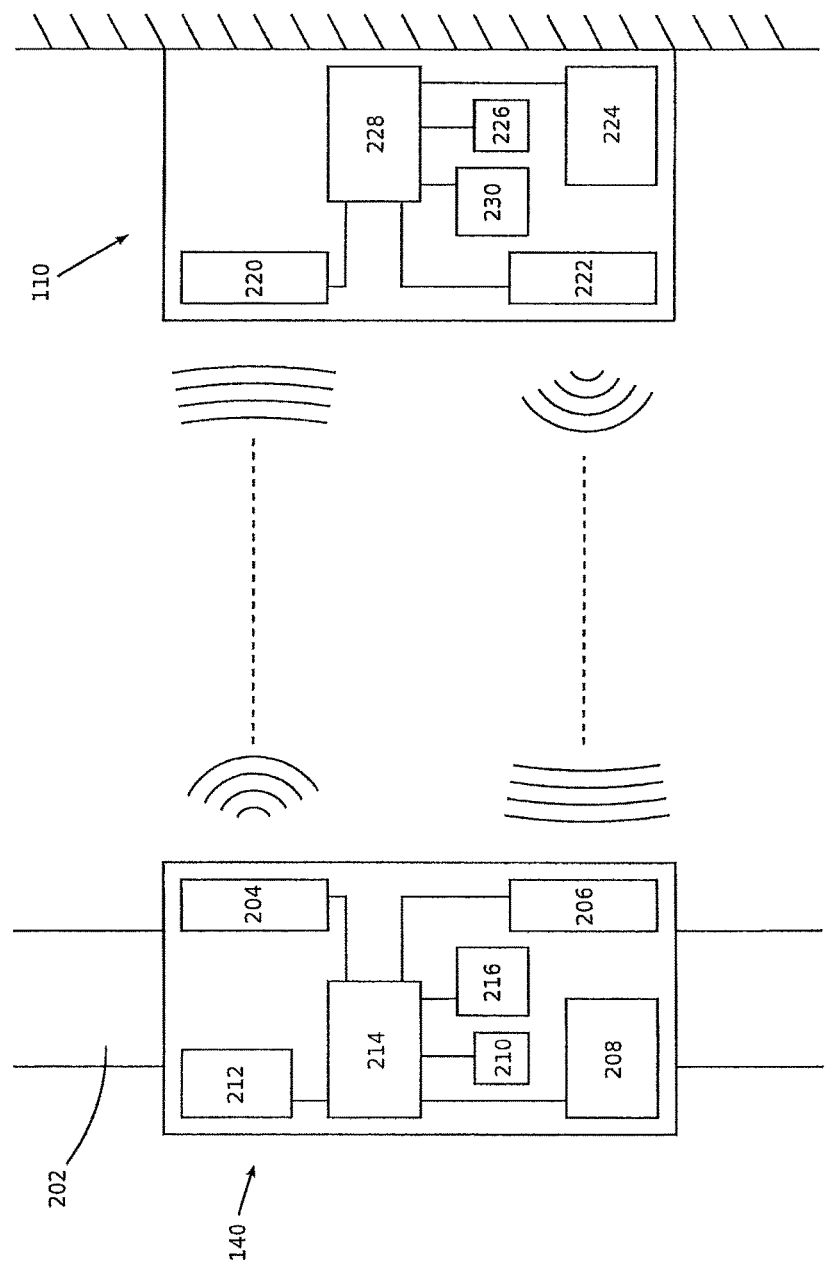
FIG. 2 schematically illustrates a mobile unit and a base unit.

FIG. 2 schematically illustrates a mobile tag 140 and a base station 110 in communication with each other. The base station 110 is fixed to a static structure of the building such as a wall, floor or ceiling. It has a receiver 220 and a transmitter 222. These may be any kind of wireless transmitter and receiver, but most conveniently ultrasound or radio frequency (RF) electromagnetic communication are used. Ultrasound is advantageous in care environments as electromagnetic waves can interfere with other equipment in the building. Ultrasound also does not penetrate the walls and so interference between base stations or from background noise is reduced compared with electromagnetic transmissions. Combinations of ultrasound and electromagnetic communication may be used.

The base unit 110 includes an air pressure sensor 224 and a temperature sensor 226. These are illustrated separately, but in practice the two sensors could be combined on a single sensor circuit. The base unit 110 also includes a processor 228 and memory 230. The processor 228 controls the transmitter 222 and receiver 220 for transmitting and receiving data and also reads data from the pressure and temperature sensors 224, 226. Memory 230 may be used during the processing procedure and may also store historical data and/or preloaded values such as predetermined values or thresholds for use in calculations and/or database structures (which may be populated or unpopulated with data). All of these data values may be updated during the course of operation.

The mobile unit or tag 140 is mounted on a strap 202 which can be used to attach the tag 140 to a person or object. In some preferred embodiments, the strap 202 is an arm band. The tag 140 has a transmitter 204 and a receiver 206. As with the base unit 110, these may be ultrasound transducers or RF antennae or combinations of both. The tag 140 also has an air pressure sensor 208 and a temperature sensor 210 similar to the base station 110. Again, the transmitter 204, receiver 206, pressure sensor 208 and temperature sensor 210 are all operated by a processor 214 which again has a memory 216 available for use. Additionally, a motion sensor 212 is provided (also connected to the processor 214) for use as described below.

For the pressure sensors and temperature sensors 208, 210, 224, 226 the units 110, 140 may use the SCP1000 from VTI and/or the MS5607 from MEAS Switzerland. These devices are low power, relatively inexpensive and can provide a height measurement accurate to within 10 cm. Both units also incorporate a temperature sensor.

First the overall infrastructure will be described with reference to FIG. 1. The description below is given in relation to a care environment where the tags 140 are attached to patients and the system is arranged to detect emergency situations when a patient collapses. A number of tags 140a-d are shown in different locations within the floor.

One or more base stations (base units) 110 are provided per floor 100 of a building, each of which contains an air pressure sensor 224 (shown in FIG. 2). The base stations 110 are statically located, i.e. they are at known fixed positions. The height above the floor of each base station 110 is known. The base station 110 samples the air pressure at regular time intervals. The sampling interval may depend on whether the unit 110 is battery powered or externally powered.

A tag (mobile unit) 140 is attached to a patient, e.g. via an arm band 202. The tag 140 also contains a pressure sensor 208 (shown in FIG. 2). The air pressure at the tag 140 is transmitted, either via ultrasound (US) or via radio frequency electromagnetic radiation (RF), and the system calculates the difference in air pressure between the tag 140 and the base station 110.

The altitude H is given by $$H = \frac{T}{G}\left[1 - \left(\frac{P}{P_0}\right)^{\left(\frac{GR}{g}\right)}\right] \quad (1)$$

where:
T is the temperature in Kelvin,
P is the pressure,
$P_0$ is a reference pressure at a fixed height,
G=−dT/dH is the negative of the temperature gradient,
R is the specific gas constant, and
g is the acceleration of gravity.

It can be assumed that the temperature within the vicinity of a pressure base unit is constant, or alternatively the system can compensate for it as a function of height based on the fact that hot air rises to the ceiling.

If all pressure base units are at the same height, that height and the corresponding pressure may be used as the reference height and pressure. In general, if the base units are at different heights, each unit must convert its measured pressure to a reference pressure at a common reference height (e.g. at the floor).

The temperature gradient may also be measured by using temperature sensors at different heights, e.g. at the floor and at the ceiling (or at the highest relevant height for the installation).

For the calculation of height differences within rooms, the above formula can be approximated as:

$$\Delta H = -\left(\frac{R}{g}\right) \cdot T \cdot \left(\frac{\Delta P}{P}\right) \quad (2)$$

where P is the reference pressure and ΔP is the pressure difference between the mobile unit and the base unit.

Equation (2) is a low power variant of equation (1) which may be simpler to implement in mobile units.

Hence, the air pressure measurements in the tag 140 and in the base station 110 provide a measure of the height difference between the two. Knowing the height of the base station 110 above the floor, the height of the tag 140 above the floor can be deduced. In particular, it can be determined whether the tag 140 (and the patient) is possibly lying on the floor or not.

The air pressure measurements are associated with considerable noise. For example, the pressure in the region of the sensor will be continually varying due to the constant movement of air due to movement of people, opening of doors, circulation of air caused by fans, etc. Signal conditioning such as averaging over multiple samples, low-pass filtering, or Kalman filtering may be applied in order to get a robust measure of the height above the floor.

The air pressure sensor readings may inherently drift slowly over time. Using multiple base stations 110 with air pressure sensors 224 on the same floor 100, this drift can be averaged out to provide a reference air pressure for the floor (assuming the drift is of a random nature, the drifts from each base station will cancel out when averaging over several base stations).

Drift in the air pressure sensors 208 in the tags 140 can be compensated in a number of ways. Some tags 140 include a motion sensor 212 that can be used to make the tag 140 enter a sleep mode when the tag 140 is stationary. In this mode, the air pressure can be sampled occasionally to compensate for drift. The process of air pressure calibration and drift compensation can be preformed in the background even though the mobile unit is stationary (in the case where it has a motion sensor and would otherwise be asleep to save power).

In some embodiments, when the tag is stationary (as indicated for example by the motion sensor), the tag can perform the role of a base station, communicating with the other base stations and improving the reference pressure estimation and saving cost in the infrastructure.

Another way to compensate for drift in the sensors of the mobile tags 140 is to assume a height band when the system detects motion from room to room. For example, a tag 140 attached to a patient's arm can be assumed to be in a rather narrow height band if one can determine that the patient is walking. Such an arrangement is illustrated in the corridor 108 of FIG. 1 where mobile unit 140*d* is passing along the corridor. It should be noted that although two base units 110 are shown in the corridor 108, only one base unit 110 is required for this method of calibration. When the unit 110 detects that the tag 140*d* is in close proximity (e.g. within a threshold distance), it determines that the patient wearing tag 140*d* is in the corridor in the vicinity of the base unit 110 and is therefore almost certainly walking. It can therefore assume that the tag 140*d* is at some predetermined height. The predetermined height will vary from patient to patient (according to the patient's height) and is preferably stored in a database on the central computer 130. The unit 110 can contact the central computer 130 (either through a direct connection or over a network and either wired or wirelessly) to request the predetermined height for that tag 140*d*. Each tag has a unique identifier which can be read by base unit 110 and sent to the central computer 130. The central computer looks up the identifier in its database and returns the appropriate predetermined height to base unit 110. Alternatively all calibration calculations can be performed on the central computer 130 which can then return calibration values (pressure and/or height) to the base station 110.

If the tag is capable of receiving data, base unit 110 can send calibration data (e.g. a current height and/or a corrected pressure reading) to the tag 140 so that the tag 140 can recalibrate itself. In an alternative arrangement, the tag 140 could have the predetermined height programmed into it, e.g. stored in memory 216 (which could be random access memory, flash memory or similar). An on board processor unit 214 can perform the recalibration calculations. If the tag 140 is not set up to receive incoming data or instructions then the unit cannot be instructed to recalibrate. Instead, the tag 140*d* sends its pressure data as normal to the base unit 110 and the base unit 110 (or the central computer 130) determines an error between this reading and the reading that would be expected for the predetermined height. This determined error can be stored (e.g. in a database on central computer 130) alongside the unique identifier for tag 140*d* and used to apply a correction to all data received from tag 140*d*. Every time the tag 140*d* passes through a recalibration zone, the calculation can be performed again and the database can be updated with corrected data.

Another way to compensate for drift is to take advantage of zones instrumented for full 3D positioning to calibrate the air pressure reading from the tag 140. Such zones do not rely on any pressure data in order to determine an accurate height for the tag 140. These zones can be deployed for the purpose of general 3D positioning as illustrated in room 104 of FIG. 1 which has three base units 110 attached to the walls and preferably has a further base unit 110 mounted in the ceiling or floor to provide an accurate z-coordinate (i.e. height above the floor). Calibration can be performed in a manner similar to that described previously.

Where the tag 140 is constrained to move through portals, e.g. doors, narrow corridors, etc, height estimation infrastructure may be deployed specifically to provide an accurate height measure. For example a series of receivers (which could be a base unit 110) arranged in a vertical array could simultaneously detect the proximity of a tag 140 as it passes by. The receiver which receives the strongest signal is determined to be the receiver at the closest height to that of the tag 140 thereby providing a simple yet accurate height detection method. If the tag is fitted with two-way communication, the tag can be instructed to enter a frequent update mode to provide accurate position estimation, for example to catch the exact moment when the tag 140 moves through a door.

Fall detection (e.g. the collapse of a patient) can, in the simplest embodiment, be detected simply on the basis of the height of a tag 140 being detected at or near the floor. However, there may be other reasons for a tag being at or near the floor, such as a patient bending down to pick something up or to access a low drawer or cupboard. Therefore a system relying solely on the current height of a tag is liable to trigger false positive alarms, i.e. the system could raise an alarm when the situation does not require it. Such a system is however reasonably robust to false negatives, i.e. it should reliably detect most situations where a patient has collapsed to the floor and correctly raise an alarm.

In a slightly more advanced system, fall detection can also be triggered by a sudden drop in height, independent of the reference pressure in the base station 110. The mobile unit 140 can raise the alarm itself based solely on its own data. However, the base station 110 can provide extra information about the starting height and finishing height of the tag. For example, the base station 110 can confirm that the tag actually ended up on the floor. An intelligent system can combine these pieces of information and raise an alarm based on the sudden drop in height together with the information that the finishing height is at or near floor level.

In yet more advanced systems, the indoor real time location system may additionally have zoning within rooms. For example, as shown in room 104 of FIG. 1, the system can identify different areas within the room. Such areas may include areas containing beds, sofas, chairs, stairs, etc that can be associated with typical patient/tag heights, and can provide additional filtering information for providing reliable alarms. As shown in FIG. 1, two special zones have been identified (and programmed into the system) in room 104. The first zone 120 is a zone containing a bed 122. When a patient is lying on the bed 122, a tag 140 can be expected to be within a predictable height band and can be expected to remain at that height for some time. A second zone 124 contains a table 126 and four chairs 128. Again, tags 140 within this zone 124 can be expected to remain mostly within a certain predictable height band, but will be prone to sudden rises and falls as people sit down or get up. The heights of the tags 140 should not however end up at floor level. The system may also combine time information with the spatial zones, for example time periods may be identified when a person is expected to be in bed 122 or dining at table 126.

As shown in room 107 of FIG. 1, an intelligent building may be equipped with a number of other sensors which can feed data into the position detection system and can be used in determining alert situations. Room 107 contains a motion sensor 150 (e.g. an infrared, ultrasound or radar motion detector such as may be used in a burglar alarm system), a light switch sensor 152 which indicates the current state (on/off) of the light, and a door sensor 154 which indicates whether the door is open or closed. It will be appreciated that these are just examples of sensors which could be used and many others could just as easily be incorporated into the system.

With all of this sensor data available to the system, substantial logic can be built involving all available sensor readings, e.g. air pressure (at the tag 140 and base units 110), ultrasound and/or RF signals from the tags 140 and other indicators such as telephone activity, motion evidence from a burglar alarm, operation of light switches, opening of doors, and other sensors in the intelligent building. It will be appreciated that the fall detection alarm needs to be reliable. In a home care setting, there is a high cost of false positives as emergency procedures will be initiated when the alarm is set off. Likewise, false negatives may be disastrous for the persons not getting the proper attention. In general, the more information that is available, the more reliably the situation can be determined.

It will be appreciated that indoor real time location systems can provide additional information like motion detection via Doppler shift that can also be used to verify the fall detection alarm.

In some situations, the logic for determining an alert situation can be significantly different, depending on the location. In particular, there could be zones for stairs with dedicated logic such that there will be no alarm when the tag descends towards (and through) the floor level. At the same time, within a stair zone, an alarm should be issued if the height remains constant, regardless of the height; or if it reduces too quickly.

In general, the air pressure sensors can be used to allow three dimensional positioning in an infrastructure deployed for two dimensional positioning. This set up is not only useful for the fall detection case outlined above, but can be used in all situations where three dimensional positioning is useful. The cost benefits of using the pressure sensors in place of additional ultrasound or RF base units still apply in such situations.

It will also be appreciated that the above principle of using an air pressure sensor to detect the height of a mobile unit 140 can be combined advantageously with any RTLS independent of the type of positioning principle deployed. Further, the tags 140 and base stations 110 described above can interact easily with existing tags (without pressure sensors) or with two dimensional infrastructure, simply without using the pressure information. Similarly, existing two dimensional infrastructure can be upgraded easily and conveniently simply by adding pressure sensors to existing base units or by replacing old base units with new ones. Such upgrades need not involve installation of additional units to provide full three dimensional positioning.

Although this invention has been shown and described with respect to the detailed embodiments thereof, it will be understood by those skilled in the art that various changes in form and detail thereof may be made without departing from the spirit and the scope of the invention.

What is claimed is:

1. A monitoring system, comprising:
   one or more mobile units; and
   a three dimensional position determination system arranged to determine three dimensional coordinates of the one or more mobile units, said system comprising at least two zones;
   wherein the system is arranged to determine which zone a selected one of the one or more mobile units is in based on its horizontal position; and
   wherein in one of said zones the system is arranged to raise an alarm when the rate of change of a vertical coordinate of the selected one of the one or more mobile units is less than a predetermined value; and
   wherein the position determination system comprises one or more fixed base units, wherein the system is arranged to determine the horizontal position of a mobile unit of the one or more mobile units based on the proximity of said mobile unit to at least one base unit and wherein the system is arranged to determine the height of said mobile unit based on the air pressure sensed at the mobile unit and the air pressure sensed at one or more of the base units.

2. The monitoring system as claimed in claim 1, wherein in another of said at least two zones the system is arranged to raise an alarm when the rate of change of a vertical coordinate of a mobile unit is greater than a predetermined value.

3. The monitoring system as claimed in claim 1, wherein the position determination system comprises a plurality of base units and wherein the system is arranged to determine a reference air pressure based on an average of the air pressures sensed at each of the plurality of base units.

4. The monitoring system as claimed in claim 1, wherein the position determination system comprises at least one height reference base unit and wherein the system is arranged such that when a mobile unit is determined to be within a certain proximity of said height reference base unit the system determines that the mobile unit is at a predetermined mobile unit reference height.

5. The monitoring system as claimed in claim 4, wherein in response to said proximity determination, the system instructs the mobile unit to perform a calibration based on the mobile unit reference height.

6. The monitoring system as claimed in claim 1, wherein the system comprises a height calibration zone, said height calibration zone comprising a plurality of base units positionally arranged so as to be capable of determining the height of a mobile unit based on the proximity of said mobile unit to each of said plurality of base units.

7. The monitoring system as claimed in claim 6, wherein in response to said height determination, the system instructs the mobile unit to perform a calibration based on the determined height.

8. The monitoring system as claimed in claim 1, wherein the system is arranged to raise an alarm based on one or more criteria being met by a mobile unit.

9. The monitoring system as claimed in claim 8, wherein the alarm criteria depend on the current position of said mobile unit.

10. The monitoring system as claimed in claim 1, wherein the alarm is arranged to indicate an identification of said mobile unit and a current position of said mobile unit.

11. The monitoring system as claimed in claim 1, wherein said one or more fixed base units and said one or more mobile units are arranged to communicate via ultrasound.

12. The monitoring system as claimed in claim 1, wherein said base unit and said mobile unit are arranged to communicate via radio communication.

13. The monitoring system as claimed in claim 1, wherein the height determination of the mobile unit based on pressure data is combined with height determination based on proximity to the base units.

14. The monitoring system as claimed in claim 1, wherein a stationary mobile unit is arranged to act as an additional base unit.

15. A building comprising a monitoring system as claimed in claim 1, wherein said building comprising one or more monitoring zones for positioning mobile units, wherein at least one monitoring zone comprises only one base unit.

16. The building as claimed in claim 15, wherein one or more monitoring zones each correspond to a room within the building.

17. The building as claimed in claim 15, wherein said position determination system is adapted to receive data from one or more building sensors within said building, said building sensors including at least one of: a light switch sensor, a motion sensor, a door sensor and a telephone activity sensor.

18. The building as claimed in claim 17, wherein the position determination system is adapted to raise an alarm based on one or more criteria being met by a mobile unit and based on the output of said building sensors.

* * * * *